United States Patent
Boesel et al.

(10) Patent No.: US 10,660,631 B1
(45) Date of Patent: May 26, 2020

(54) PEDICLE SCREW MOUNTED RETRACTOR SYSTEM

(71) Applicant: Invictus Development & Engineering, Inc., Boca Raton, FL (US)

(72) Inventors: Blake D. Boesel, Boca Raton, FL (US); Robert P. Norton, Boca Raton, FL (US)

(73) Assignee: Invictus Development & Engineering, Inc., Boca Raton, FL (US)

( * ) Notice: Subject to any disclaimer, the term of this patent is extended or adjusted under 35 U.S.C. 154(b) by 0 days.

(21) Appl. No.: 16/218,641

(22) Filed: Dec. 13, 2018

(51) Int. Cl.
    *A61B 17/02*     (2006.01)
    *A61B 17/88*     (2006.01)
    *A61B 17/70*     (2006.01)

(52) U.S. Cl.
    CPC ...... *A61B 17/0206* (2013.01); *A61B 17/7077* (2013.01); *A61B 2017/0256* (2013.01)

(58) Field of Classification Search
    CPC ............ A61B 17/0206; A61B 17/7077; A61B 2017/2056
    USPC ......... 606/279, 307, 308, 323, 327, 328, 90, 606/105, 86 A; 600/201, 204, 205, 208, 600/210, 213, 215, 222, 226
    See application file for complete search history.

(56) References Cited

U.S. PATENT DOCUMENTS

| | | | |
|---|---|---|---|
| 6,520,907 B1 * | 2/2003 | Foley ..................... | A61B 17/02 600/114 |
| 8,152,720 B2 | 4/2012 | Loftus et al. | |
| 8,182,519 B2 | 5/2012 | Loftus et al. | |
| 8,317,692 B2 | 11/2012 | Loftus et al. | |
| 8,574,154 B2 | 11/2013 | Loftus et al. | |
| 8,617,063 B2 | 12/2013 | Loftus et al. | |
| 8,888,822 B2 | 11/2014 | Loftus et al. | |
| 8,894,573 B2 | 11/2014 | Loftus et al. | |
| 9,622,795 B2 | 4/2017 | Reitblat et al. | |
| 10,426,454 B2 * | 10/2019 | Ponmudi ............. | A61B 17/0206 |
| 2003/0083688 A1 * | 5/2003 | Simonson .......... | A61B 17/0218 606/191 |
| 2005/0234304 A1 * | 10/2005 | Dewey ............... | A61B 17/0206 600/210 |
| 2009/0036746 A1 * | 2/2009 | Blackwell .......... | A61B 17/0206 600/219 |
| 2010/0113885 A1 * | 5/2010 | McBride .................. | A61B 1/32 600/224 |
| 2012/0197300 A1 | 8/2012 | Loftus et al. | |

(Continued)

*Primary Examiner* — Pedro Philogene
*Assistant Examiner* — David C Comstock
(74) *Attorney, Agent, or Firm* — David L. King (57) ABSTRACT

A pedicle screw mounted retractor has a split tube body that has a central tube longitudinally split into two split halves, a first half portion and a second half portion. The split halves form a central working portal. Each half portion has a cylindrical retractor tube appended on a side along an external surface. Each cylindrical retractor tube has a flange with a post extending at or near a proximal end. The pair of cylindrical retractor tubes is configured to pass onto and over a tower or extended top threaded post of a pedicle screw prepositioned in a pair of vertebrae for retracting the vertebrae. The central working portal has at least a 20 mm diameter in a closed and abutted orientation of the first and second split halves. In one embodiment, the central working portal has a 22 mm diameter in the closed and abutted orientation.

11 Claims, 10 Drawing Sheets

(56) References Cited

U.S. PATENT DOCUMENTS

| | | | |
|---|---|---|---|
| 2013/0053896 A1* | 2/2013 | Voyadzis | A61B 17/708 606/279 |
| 2014/0275793 A1 | 9/2014 | Song | |
| 2015/0164569 A1 | 6/2015 | Reitblat et al. | |
| 2016/0038195 A1* | 2/2016 | Genovese | A61B 17/7082 606/79 |
| 2017/0143323 A1* | 5/2017 | Cryder | A61B 17/025 |
| 2017/0189080 A1 | 7/2017 | Reitblat et al. | |
| 2019/0290335 A1* | 9/2019 | Biester | A61B 17/3423 |

* cited by examiner

PEDICLE SCREW MOUNTED RETRACTOR SYSTEM

TECHNICAL FIELD

The present disclosure relates to methods and devices for retracting tissue in a surgical procedure to allow access to the surgical site, more particularly to a method and device employing a pedicle screw mounted retractor.

BACKGROUND OF THE INVENTION

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site. One typical prior art retractor system includes a plurality of blades coupled to a retractor frame. In use, the blades may be inserted into an incision and then retracted to displace tissue surrounding the incision exposing the surgical site. To minimize trauma to the tissue, this tissue displacement should be refined and controlled. However, current retractor systems do not provide desired control of the distraction. More particularly, the devices currently in use are mechanically coupled so the surgeon has limited ability to feel the resistance at the blades or to rotate the blades affixed to the retractor arm independently. This limited control takes away the skilled surgeon's ability to finely adjust the movement of the retractor blades.

There has been considerable development of retractors and retractor systems that are adapted for use in less invasive procedures. Standard hand-held surgical retractors are well known in the prior art and can be modified to fit the contours of these small incisions. Typical retractors are also positioned into the soft tissue and are levered back to hold the wound open, frequently requiring re-positioning if they dislodge, obstruct the physician's view, or interfere with access to the surgical site. Minimally invasive surgical approaches are being applied to orthopedic spine surgery and more recently to spine surgery. Surgery on the spine involves multiple layers of soft tissue, bone, ligaments, and nerves.

In a typical spine fusion, at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. The difficulty arises upon the introduction of a length of rod into a very small incision with extremely limited access and visibility. A single level fusion may require a 30-40 mm rod to be introduced into a 1 cm incision and a multilevel fusion may require a rod several inches long to fit into a 1 cm incision. For this reason, it is important that the minimal incision be maintained in an open and accessible condition for introduction of the rod.

Minimally invasive surgery offers significant advantages over conventional open surgery. First, the skin incision and subsequent scar are significantly smaller. By using more than one small incision rather than one large incision, the need for extensive tissue and muscle retraction may be greatly reduced. This leads to significantly reduced post-operative pain, a shorter hospital stay and a faster overall recovery.

Therefore, there is a need for improved methods and devices that can be used for retracting tissue to provide access to the surgical site while minimizing trauma to soft tissue surrounding an incision.

SUMMARY OF THE INVENTION

A pedicle screw mounted retractor has a split tube body. The split tube body has a central tube longitudinally split into two split halves, a first half portion and a second half portion. The split halves form a central working portal. Each half portion has a cylindrical retractor tube appended on a side along an external surface. Each cylindrical retractor tube has a flange with a post extending at or near a proximal end. The pair of cylindrical retractor tubes, one on each split half is configured to pass onto and over a tower or extended top threaded post of a pedicle screw prepositioned in a pair of vertebrae for retracting the vertebrae. The central working portal has at least a 20 mm diameter in a closed and abutted orientation of the first and second split halves. In one embodiment, the central working portal has a 22 mm diameter in the closed and abutted orientation.

Each post has a snap on detent configured to receive a handle. The pedicle screw mounted retractor further has a pair of handles, each handle with an opening to secure the handle to the post. The pair of cylindrical retractor tubes and flanged posts are oriented diametrically opposed form the central working portal.

The pedicle screw mounted retractor further has a set of central dilator tubes. The set of central dilator tubes is sized to stack into each other thereby increasing in diameter to dilate an incision between the pair of pedicle screws. The split tube retractor is configured to pass onto each pedicle screw tower and the stacked central dilator tubes positioned therebetween to increase the size of the central working portal of the split tube.

The pedicle screw mounted retractor provides a novel method of distracting a pair of vertebrae. The method has the steps of inserting a pair of pedicle screws with towers or extended tops with threaded posts of the pedicle screw, one in each vertebra; dilating an incision between the pedicle screws with a set of dilator tubes; placing a split tub retractor over the towers and the dilators and sliding downwardly toward the dilated incision; and removing the set of dilators leaving the split tube retractor in place to visualize through the central working portal of the split tube retractor to verify the position and anatomy. The split tube retractor has two split halves defining the central working portal and a pair of cylindrical tubes with flanged posts and the method step of sliding the split tube retractor includes placing each cylindrical tube onto one of the inserted pedicle screws and placing the central working portal over the set of dilators and sliding downwardly toward the dilated incision. The method further has the step of placing and attaching a handle onto each post of the split halves. The method further includes the step of grasping the attached handles and distracting the vertebrae pulling the handles thereby moving the retractor split halves apart while maintaining the inserted pedicle screws parallel.

Definitions

As used herein and in the claims:

A retractor is a surgical instrument used to separate the edges of a surgical incision or wound, or to hold back underlying organs and tissues so that body parts under the incision may be accessed. The general term retractor usually describes a simple handheld steel tool possessing a curved, hooked, or angled blade and fitted with a comfortable handle, that when in place maintains the desired position of a given region of tissue. These simple retractors may be handheld, clamped in place, or suspended at the end of a robotic arm. Retractors can also be self-retaining and not need to be held once inserted by having two or more opposing blades or hooks which are separated via spring, ratchet, worm gear or other method. The term retractor is also used to describe distinct, hand-cranked devices such as rib spreaders (also known as thoracic retractors, or distractors) with which surgeons may forcefully drive tissues apart to obtain exposure. For specialized situations such as spinal surgery, retractors have been fitted both with suction and with fiberoptic lights to keep a surgical wound dry and illuminated.

Distraction means separation of joint surfaces without rupture of their binding ligaments and without displacement. Also, a method of straightening a spinal column by the forces of axial tension pulling on the joint surfaces

BRIEF DESCRIPTION OF THE DRAWINGS

The invention will be described by way of example and with reference to the accompanying drawings in which.

DETAILED DESCRIPTION OF THE INVENTION

Figure 1:
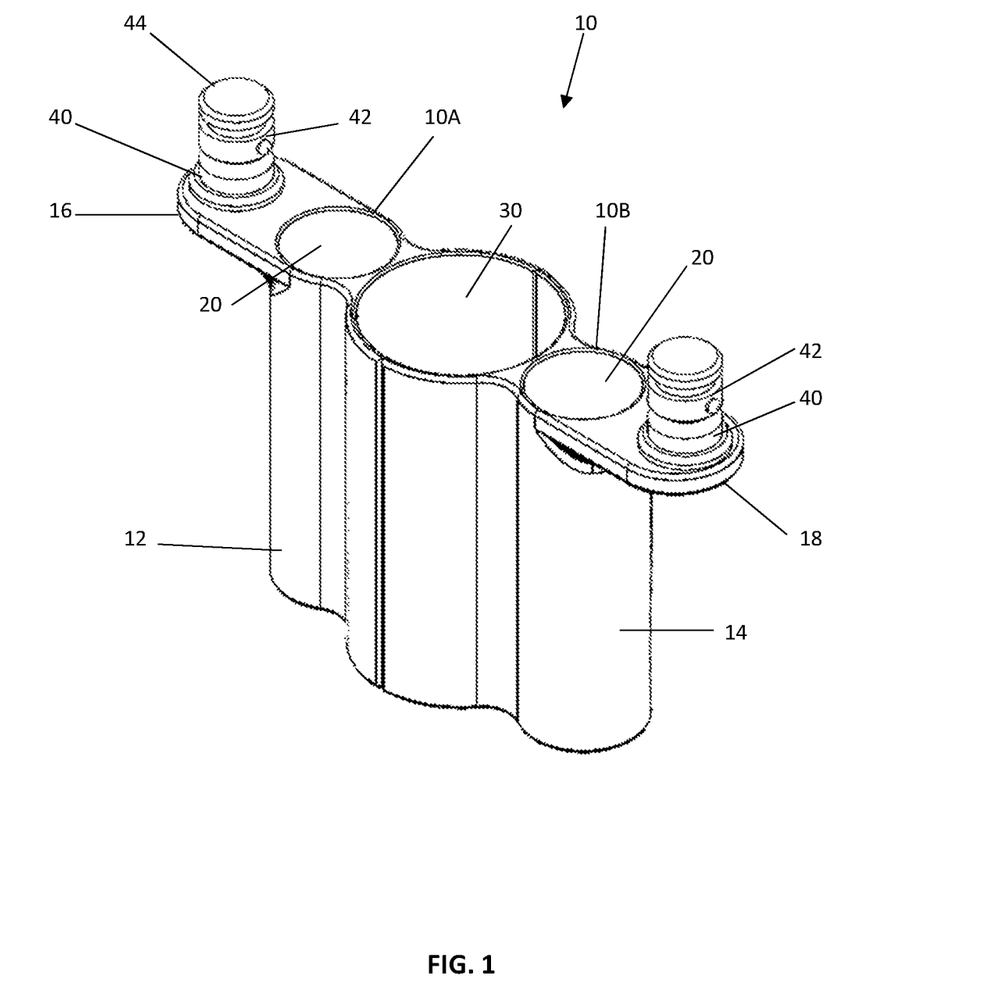
FIG. 1 is a perspective view of the pedicle screw mounted retractor of the present invention shown with the first and second split half portions in a closed position.
Figure 2:
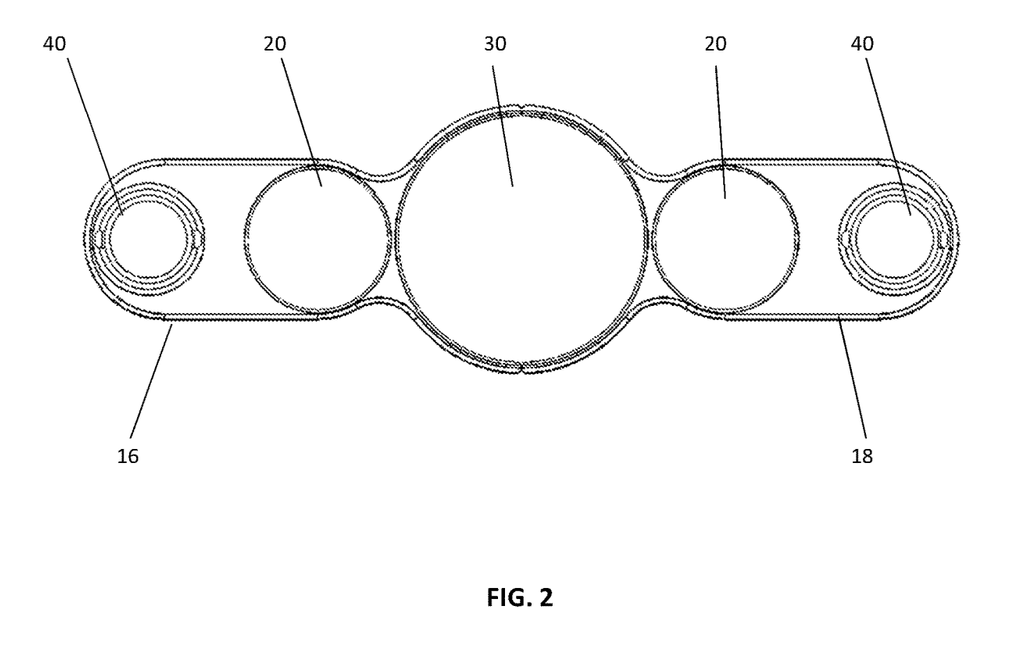
FIG. 2 is top plan view of the pedicle screw mounted retractor taken from FIG. 1.
Figure 3:
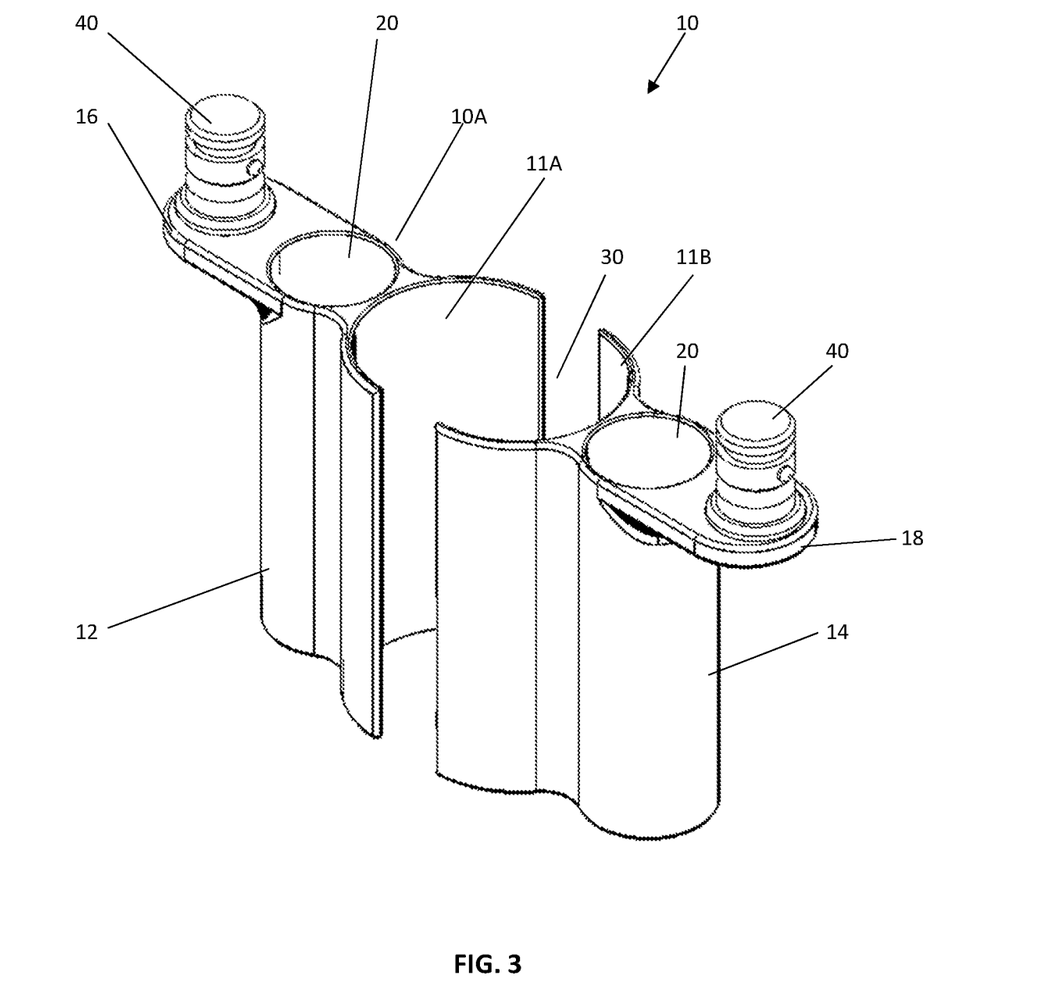
FIG. 3 is a perspective view of the pedicle screw mounted retractor of the present invention shown with the split halves in an open position.
Figure 4:
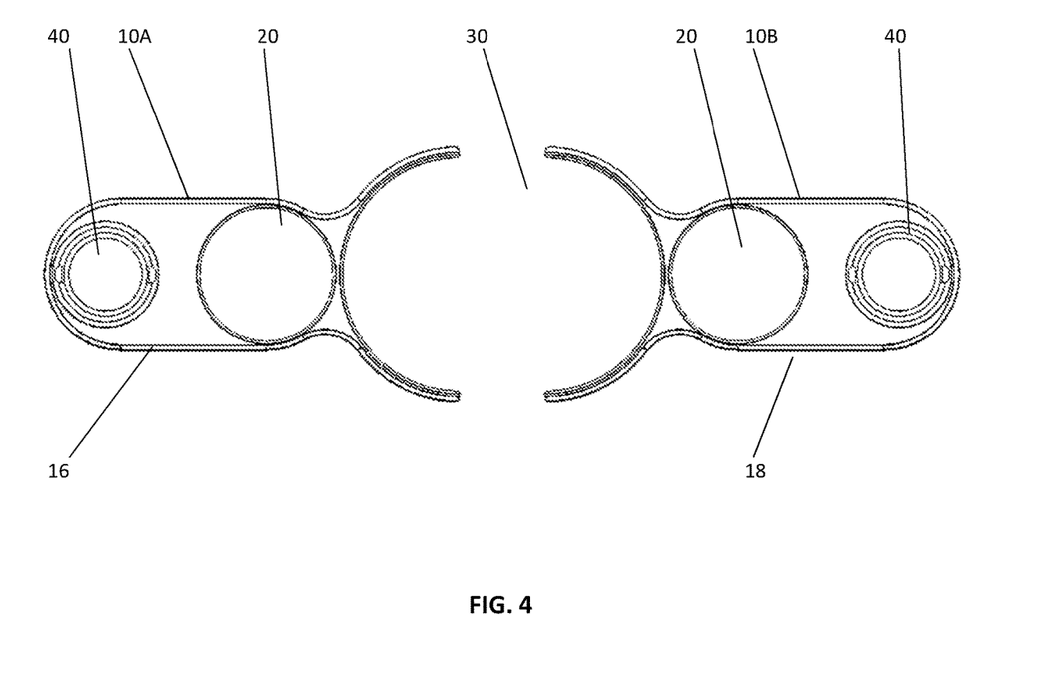
FIG. 4 is a top plan view of the pedicle screw mounted retractor of the present invention taken from FIG. 3.

With reference to FIGS. 1 and 2, the pedicle screw mounted retractor 10 is illustrated in a closed configuration. With reference to FIGS. 3 and 4, the pedicle screw mounted retractor 10 is shown in an open or split configuration.

As shown, the pedicle screw mounted retractor 10 has a split tube body having a first split half 10A and a second split half 10B. Each split half 10A, 10B forms a retractor blade. The split halves when closed as shown in FIG. 1 form a central working portal 30. On each side of the central working portal 30 on an exterior surface is appended a cylindrical retractor tube 12 and 14. Each cylindrical retractor tube 12, 14 has an opening 20 that extends from a proximal end to a distal end of each retractor tube. The circular opening 20 is configured to fit over a tower or extension of a pedicle screw when inserted in a vertebra. As illustrated, at a proximal end of the cylindrical retractor tube 12, 14 on each split half 10A, 10B is shown a flange at the top surface, this outwardly extending flange 16, 18 has a post 40 at a far end of the flange disposed from the central working portal 30. This post 40 is shown protruding upwardly and is configured to receive a handle 50. Each post 40 has a snap detent 42 and release button 44 at the top of the post 40.

With reference to FIG. 2, the top view of the pedicle screw mounted retractor 10 showing the two split halves 10A, 10B in the closed position and showing the openings 20 disposed on opposite sides of the split halves 10A, 10B. These diametrically opposed cylindrical retractor tubes 12, 14 are ideally suited to fit over inserted pedicle screw towers. As shown, in the closed position, the flanges 16, 18 are also aligned through a central axis of the pedicle screw mounted retractor 10.

In FIG. 3, the split halves 10A, 10B are shown separated, as shown the split halves have an internal surface 11A, 11B. These internal surfaces 11A, 11B are designed to define the central working portal 30 which can be extended larger when the pedicle screws are positioned apart allowing the cylindrical tubes 12, 14 to be mounted over the pedicle screws. The split halves 10A, 10B can be separated by the distances required by the surgeon as he retracts or distracts the vertebrae.

FIG. 4 demonstrates the pedicle screw mounted retractor 10 in the fully opened position. An interesting aspect of the present invention is that as the retractor 10 extends open, each split half 10A, 10B can move independently while the pedicle screws remain parallel relative to the other.

Figure 5:
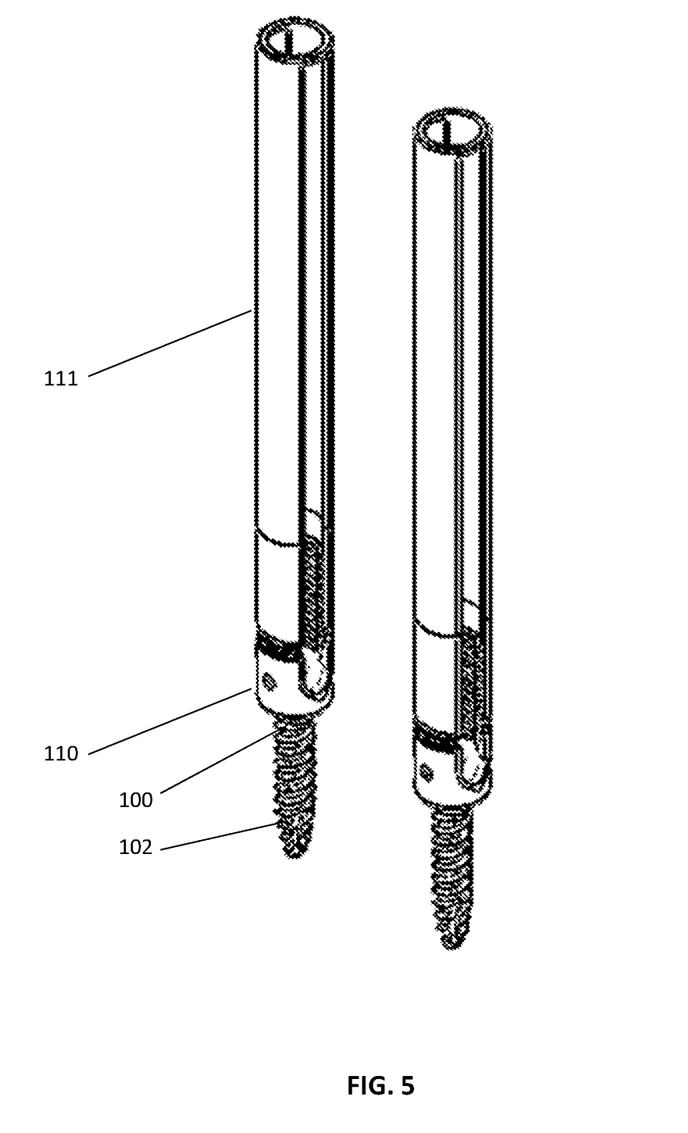
FIG. 5 shows a pair of exemplary pedicle screws illustrated in a spaced apart perspective to represent a relative position as if each threaded shank has been positioned into a vertebra of a spine.
Figure 6:
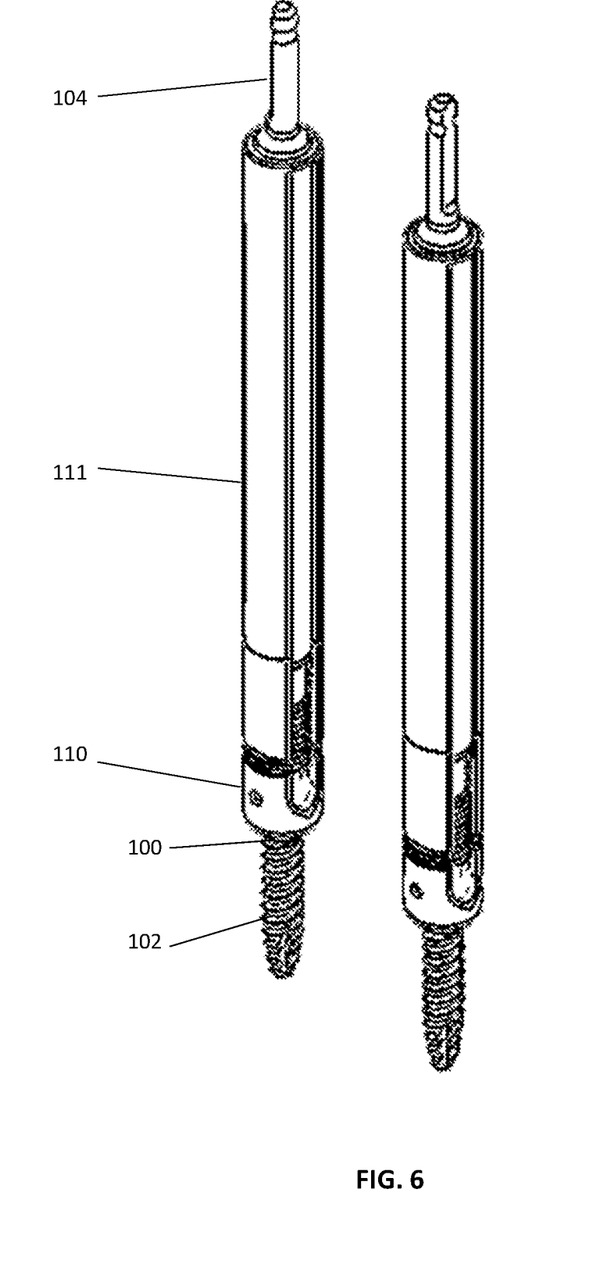
FIG. 6 is the pair of pedicle screws shown with tread in fixation posts to lock polyaxial motion of the tulips extending from the heads oar proximal ends of the pedicle screws.

FIG. 5 shows a typical exemplary pedicle screw system. The pedicle screw 100 has a tower or extended portion 111 extended above the tulip 110. The tower 111 has internal threads configured to receive a fixation post 104 as illustrated in FIG. 6. As shown, the threaded portions 102 of the pedicle screws 100 are spaced to represent a positioning between adjacent vertebrae, the vertebra are not shown for clarity. Once the pedicle screws 100 are in position the fixation posts 104 are provided that slide internally of the towers 111. In this position, the tulips 110 can be locked into place with the adjacent vertebrae. The present invention retractor 10 is configured to universally fit virtually any pedicle screw system.

Figure 7:
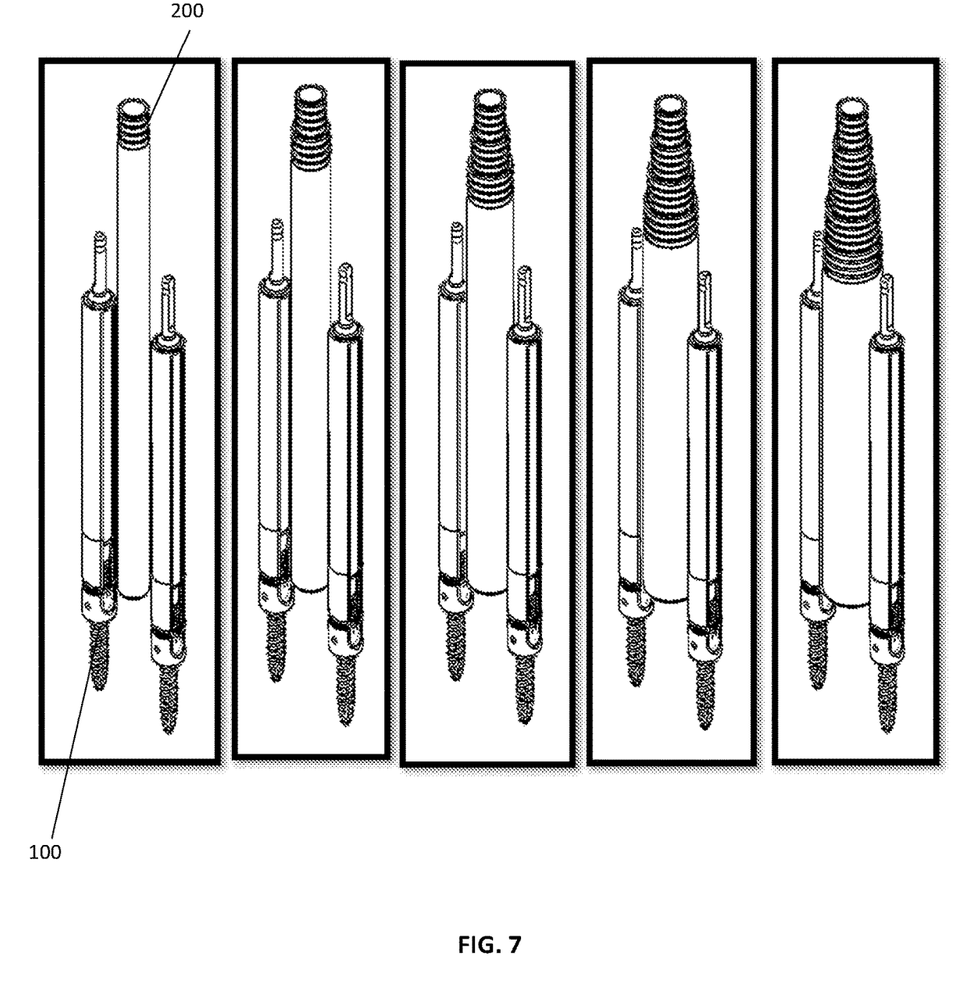
FIG. 7 is a sequential view of dilators of increasing diameters being placed between the pair of pedicle screws to demonstrate how the inserted screws can be pushed apart to space the vertebrae to which each screw is affixed, the vertebrae not shown for clarity.
Figure 8:
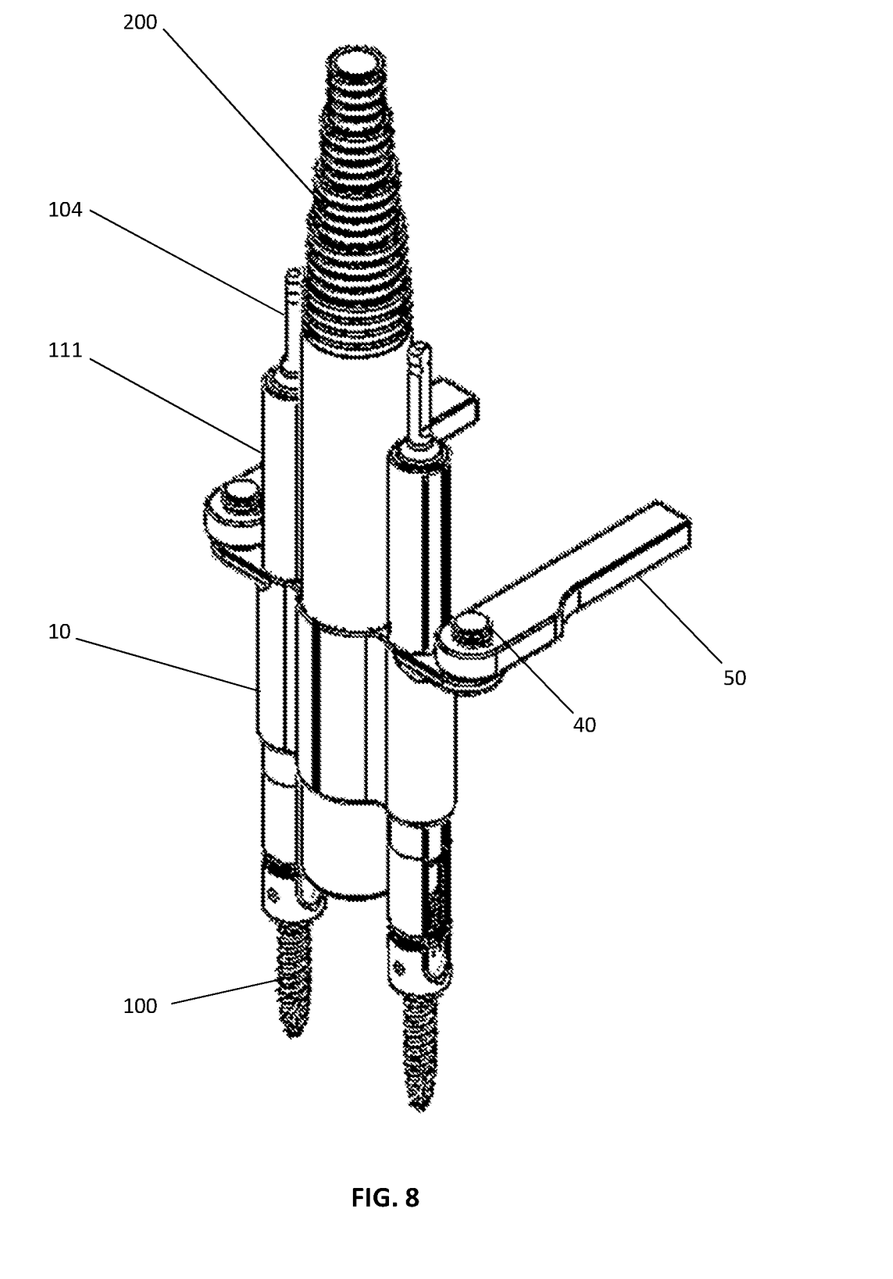
FIG. 8 illustrates a view wherein the pedicle screw mounted retractor of the present invention with handles attached is shown mountably placed over the pair of inserted pedicle screws and the plurality of stacked dilator tubes.

Once the pedicle screws 100 are locked into adjacent vertebrae, the soft tissue can then be dilated by using a plurality of stacked sequential dilator tubes 200, as shown in FIG. 7. The surgeon will first place a smaller diameter tube 200 between the two pedicle screws 100 and increasingly stack larger diameter tubes 200 over each progressively smaller tube such that the larger diameter tubes continue to push the tissues out dilating the incision. FIG. 8 shows the set of dilators 200 inserted in the central working portal 30 of the pedicle screw mounted distractor 10 of the present invention that has been slid over the towers 111 holding the pedicle screws 100 and vertebrae in a parallel configuration. As shown in FIG. 8, the retractor assembly 10 has a handle 50 positioned onto each post 40.

Figure 9:
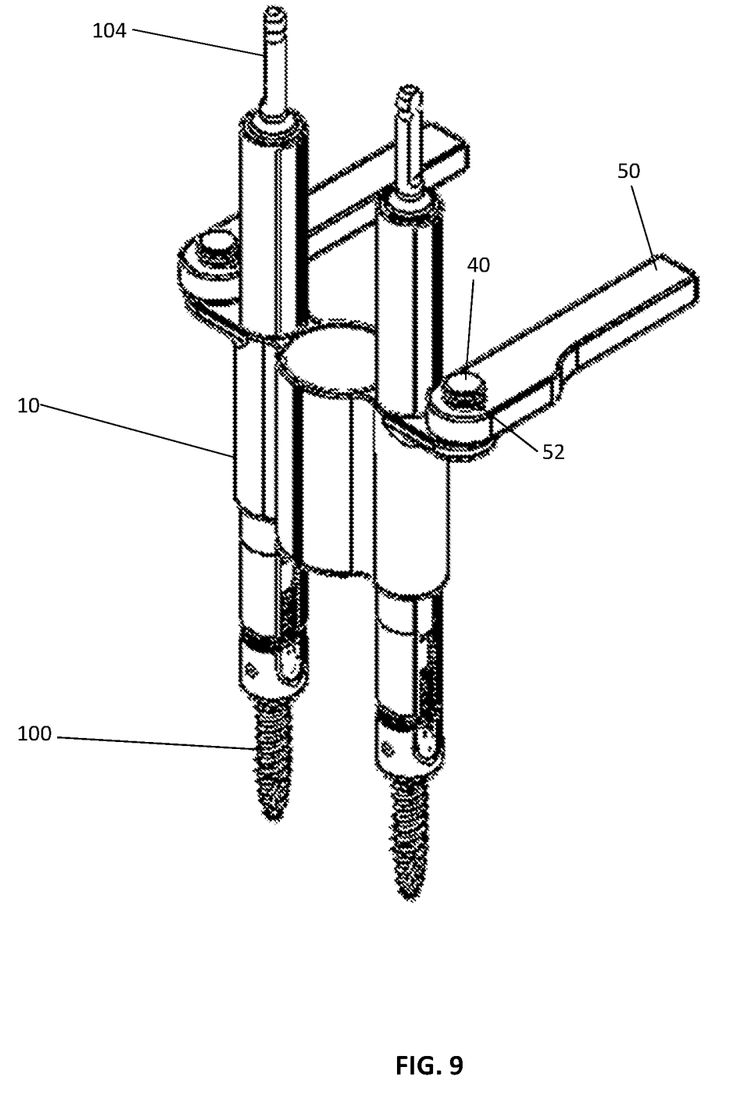
FIG. 9 is a view taken from FIG. 8 showing the stacked dilator tubes removed leaving the pedicle screw mounted retractor of the present invention on the pair of pedicle screws allowing the surgeon to observe and verify the proper position and anatomy.
Figure 10:
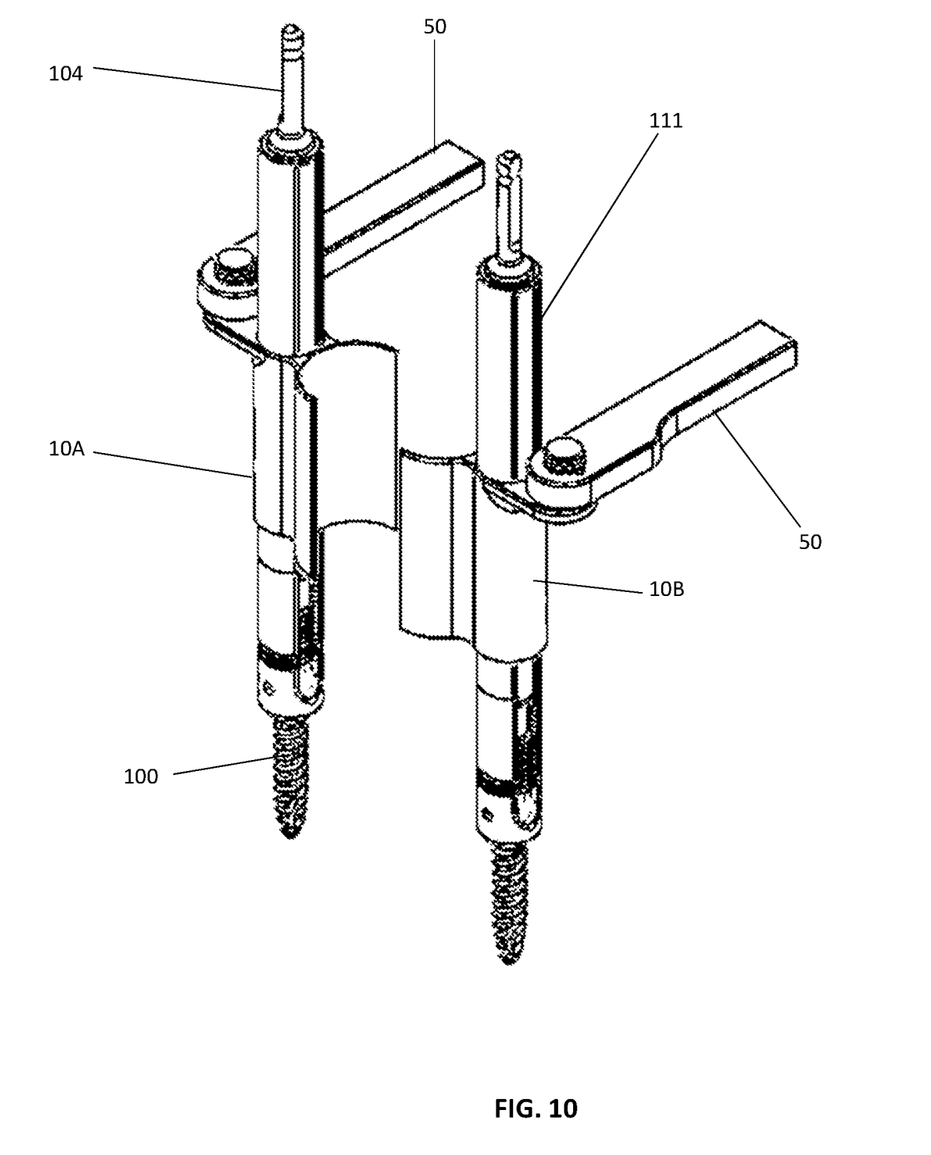
FIG. 10 is the view from FIG. 9 but wherein the retractor is pulled open by handles while the retractor tubes mounted onto the extension s or towers maintain the inserted pedicle screws parallel as the tubes distract the vertebral bodies.

With reference to FIG. 9, once the dilator tubes 200 have been removed, the surgeon can visualize into the central working portal 30 to see that the position and anatomy are correct for distraction of the vertebrae. Once the surgeon is satisfied that the positioning is correct, the physician, using the handles 50, can distract the vertebrae spacing the pedicle screws 100 apart. The cylindrical retractor tubes 12, 14 are securely positioned over the towers 111 so that they assist the surgeon in moving the assembly together in a parallel fashion not jeopardizing the threaded insertion into the vertebrae such that the pedicle screws 100 do not become loosened or dislodged during a procedure. As shown in FIG. 10, while opening, the screws 100 stay parallel with the tubes 12, 14 distracting the vertebral bodies.

For the purpose of this invention, none of the vertebral bodies are illustrated, however, it is assumed that one skilled in the art appreciates the location of the pedicle screws into the adjacent vertebrae. As shown, the split halves 10A, 10B and handles 50 provide an ideal system for distracting during the minimally invasive surgical procedure. Further, the pedicle screw mounted retractor 10 is illustrated with the split halves 10A, 10B having a cylindrical opening, with the proximal end basically flat, and the distal end basically parallel and flat. Alternatively, it is possible to have the sides 11A, 11B of each split half 10A, 10B made with a pointed retractor blade configuration that would extend slightly inward of the retractor tubes 12, 14. Although not shown, it is understood that a variety of retractor blades could be attached to the split halves 10A, 10B if so desired or the split halves could be configured in the shape of some typical retractor blades to facilitate in inserting the retractor 10 into the incision for opening and extending it during the procedure.

There are numerous pedicle screw retractors currently on the market designed to connect to two adjacent screws which have been implanted into the pedicles of the lumbar spine. Many of these retractors rely on specialized connection devices and or headless screws. The Universal Pedicle Screw Retractor System of the present invention is capable of connecting to nearly any standard, reduction, or MIS tulip pedicle screw system on the market using simple threaded posts. These threaded posts can be customized to match the required thread form of any tulip thread. While this may be unique, the novel portion of this retractor is the design of the tubular blades.

The novel design of the retractor blades themselves are designed not only to slide over the pedicle screw and threaded posts but also incorporates a central 22 mm or similar sized central working portal. It is believed that there is not another system like this currently offered in the spine market. The retractor body will not be shown as the blades are designed to connect to many different retractors currently available.

The images, as shown, for the design of this system as well as the steps taken to use it in the lumbar spine are unique compared to those currently available in the prior art.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims. The surgical access window described herein encompasses the dimensions presented and any and all variations applicable to the methods and surgical technique described directly or indirectly intended with this device.

What is claimed is:

1. A pedicle screw mounted retractor comprising:
a split tube body having a central tube longitudinally split into two split halves, a first half portion and a second half portion, the split halves form a central working portal, each first and second half portions having a cylindrical retractor tube appended on an opposite side longitudinally along an external surface of the respective half portion and each cylindrical retractor tube having a flange with a post extending at or near a proximal end, the pair of cylindrical retractor tubes, one on each first half portion and second half portion of the two split halves being configured with an opening extending from a proximal end to a distal end of each cylindrical retractor tube to pass onto and over a tower or extended top threaded post of a pedicle screw prepositioned in a pair of vertebrae for retracting the vertebrae, and wherein the distraction of the vertebrae spacing the pedicle screws apart occurs with the cylindrical retractor tubes securely positioned over the towers maintaining the pedicle screws parallel with the tubes during opening the split halves of the pedicle screw mounted retractor.

2. The pedicle screw mounted retractor of claim 1 wherein the central working portal has at least a 20 mm diameter in a closed and abutted orientation of the first and second split halves.

3. The pedicle screw mounted retractor of claim 2 wherein the central working portal has a 22 mm diameter in the closed and abutted orientation.

4. The pedicle screw mounted retractor of claim 3 wherein each post has a snap on detent configured to receive a handle.

5. The pedicle screw mounted retractor of claim 4 wherein the pair of cylindrical retractor tubes and flanged posts are oriented diametrically opposed form the central working portal.

6. The pedicle screw mounted retractor of claim 1 further comprises:
a pair of handles, each handle with an opening to secure the handle to the post.

7. The pedicle screw mounted retractor of claim 1 further comprises:
a set of central dilator tubes sized to stack into each other thereby increasing in diameter to dilate an incision between the pair of pedicle screws; wherein the split tube retractor is configured to pass onto each pedicle screw tower and the stacked central dilator tubes positioned therebetween to increase the size of the central working portal of the split tube.

8. A method of distracting a pair of vertebrae comprises:
inserting a pair of pedicle screws with towers or extended tops with threaded posts of the pedicle screw, one in each vertebra;
dilating an incision between the pedicle screws with a set of dilator tubes;
placing a split tube retractor over the towers and the dilators and sliding downwardly toward the dilated incision, wherein the split tube retractor has a split tube body having a central tube longitudinally split into two split halves, a first half portion and a second half portion, the split halves form a central working portal, each first and second half portions having a cylindrical retractor tube appended on an opposite side longitudinally along an external surface of the respective half portion and each cylindrical retractor tube having a flange with a post extending at or near a proximal end, the pair of cylindrical retractor tubes, one on each first half portion and second half portion of the two split half halves being configured with an opening extending from a proximal end to a distal end of each cylindrical retractor tube to pass onto and over a tower or extended top threaded post of a pedicle screw prepositioned in a pair of vertebrae for retracting the vertebrae, and wherein the distraction of the vertebrae spacing the pedicle screws apart occurs with the cylindrical retractor tubes securely positioned over the towers maintaining the pedicle screws parallel with the tubes during opening the split halves of the pedicle screw mounted retractor; and
removing the set of dilators leaving the split tube retractor in place to visualize through the central working portal of the split tube retractor to verify the position and anatomy.

9. The method of claim 8 wherein the split tube retractor has two split halves defining the central working portal and a pair of cylindrical tubes with flanged posts and the method step of sliding the split tube retractor includes placing each cylindrical tube onto one of the inserted pedicle screws and placing the central working portal over the set of dilators and sliding downwardly toward the dilated incision.

10. The method of claim 9 further comprises the step of placing and attaching a handle onto each post of the split halves.

11. The method of claim 10 further comprises the step of grasping the attached handles and distracting the vertebrae pulling the handles thereby moving the retractor split halves apart while maintaining the inserted pedicle screws parallel.

* * * * *